US012746348B2

(12) United States Patent
Brunner et al.

(10) Patent No.: US 12,746,348 B2
(45) Date of Patent: Sep. 29, 2026

(54) APPARATUS FOR USE IN AEROSOL DELIVERY

(71) Applicant: SENSORY CLOUD, INC., Boston, MA (US)

(72) Inventors: Robert Brunner, Glen Ellen, CA (US); Zu-Ning Chen, San Francisco, CA (US); Emerson Holladay, San Francisco, CA (US)

(73) Assignee: SENSORY CLOUD, INC., Boston, MA (US)

( * ) Notice: Subject to any disclaimer, the term of this patent is extended or adjusted under 35 U.S.C. 154(b) by 442 days.

(21) Appl. No.: 18/571,102

(22) PCT Filed: Jun. 16, 2022

(86) PCT No.: PCT/US2022/033798
§ 371 (c)(1),
(2) Date: Dec. 15, 2023

(87) PCT Pub. No.: WO2022/266325
PCT Pub. Date: Dec. 22, 2022

(65) Prior Publication Data

US 2025/0001104 A1 Jan. 2, 2025

Related U.S. Application Data

(60) Provisional application No. 63/211,633, filed on Jun. 17, 2021.

(51) Int. Cl.
*A61M 11/00* (2006.01)
*A61M 11/02* (2006.01)

(52) U.S. Cl.
CPC .......... *A61M 11/007* (2014.02); *A61M 11/02* (2013.01)

(58) Field of Classification Search
CPC ........ A61M 11/00; A61M 11/006-008; A61M 11/02; A61M 11/06; A61M 11/08
See application file for complete search history.

(56) References Cited

U.S. PATENT DOCUMENTS

D162,679 S 3/1951 Munnecke
D175,301 S 8/1955 Fisher et al.
(Continued)

FOREIGN PATENT DOCUMENTS

ES 2271692 T3 4/2007
JP H05277188 A 10/1993
(Continued)

OTHER PUBLICATIONS

Hudson RCI, "Product Catalog 2004-2005", 91 pages.
(Continued)

*Primary Examiner* — Rachel T Sippel
(74) *Attorney, Agent, or Firm* — Cozen O'Connor

(57) ABSTRACT

An apparatus for use in aerosol delivery has a housing with a first rigid shell; a second rigid shell; and a deformable band coupling the first and the second rigid shells together to allow axial translation therebetween while advantageously preventing the ingress of debris or other contaminants into the housing. The housing has a cavity sized to accommodate a spray bottle therein. Pinching the rigid shells of the housing together causes operative engagement of a piston or pump of the spray bottle to dispense an aerosol, for instance to hydrate and/or deliver a physiological salt (e.g., $CaCl_2$) to an upper respiratory tract. The housing may allow replacement of the spray bottle (e.g., sterile fill reservoir), for instance as the contents thereof are depleted. Registration features can ensure that a nozzle of the spray bottle aligns with a port in the housing.

20 Claims, 6 Drawing Sheets

(56) References Cited

U.S. PATENT DOCUMENTS

| | | | | |
|---|---|---|---|---|
| D513,797 | S | 1/2006 | Wang | |
| 7,320,415 | B2 | 1/2008 | McGuyer | |
| D562,956 | S | 2/2008 | Martinez et al. | |
| D565,713 | S | 4/2008 | Gao | |
| D752,732 | S | 3/2016 | Ansley et al. | |
| 9,540,164 | B1 | 1/2017 | Schumacher | |
| 9,573,154 | B2 | 2/2017 | Bretillot et al. | |
| D795,407 | S | 8/2017 | Skoda et al. | |
| D797,270 | S | 9/2017 | McDonnell | |
| 9,751,102 | B2 | 9/2017 | Blake | |
| D799,014 | S | 10/2017 | Suarez et al. | |
| D806,845 | S | 1/2018 | Kim et al. | |
| D820,422 | S | 6/2018 | Kim et al. | |
| D825,730 | S | 8/2018 | Servaire | |
| D831,184 | S | 10/2018 | Liang | |
| 2004/0094146 | A1 | 5/2004 | Schiewe et al. | |
| 2008/0187609 | A1 | 8/2008 | Vail et al. | |
| 2008/0230053 | A1 | 9/2008 | Kraft et al. | |
| 2010/0280466 | A1* | 11/2010 | Py | B05B 11/1004 604/290 |
| 2012/0090730 | A1* | 4/2012 | Dumont | B05B 11/0044 141/2 |
| 2017/0049977 | A1 | 2/2017 | Eicher et al. | |
| 2017/0050200 | A1 | 2/2017 | Thompson et al. | |
| 2017/0326311 | A1* | 11/2017 | Truex | G01M 3/20 |
| 2018/0085551 | A1 | 3/2018 | Krietzman | |
| 2018/0244459 | A1 | 8/2018 | Kojima et al. | |
| 2019/0105460 | A1 | 4/2019 | Edwards et al. | |
| 2020/0148459 | A1 | 5/2020 | Bartolucci et al. | |
| 2023/0062996 | A1* | 3/2023 | Jackson | A61M 11/008 |

FOREIGN PATENT DOCUMENTS

| | | | |
|---|---|---|---|
| JP | H11504567 | A | 4/1999 |
| JP | 6140577 | B2 | 5/2017 |
| WO | 2007117675 | A2 | 10/2007 |
| WO | 2009086470 | A2 | 7/2009 |
| WO | 2010065744 | A2 | 6/2010 |
| WO | 2013006809 | A2 | 1/2013 |
| WO | 2015054280 | A1 | 4/2015 |
| WO | 2017150919 | A1 | 9/2017 |
| WO | 2018227275 | A1 | 12/2018 |

OTHER PUBLICATIONS

Hudson Respiratory Care, Oxygen Therapy, Aerosol Therapy, Incentive Spirometers, Teleflex, Nov. 2011, 24 pages.

International Search Report and Written Opinion for PCT/US2022/033798 dated Oct. 5, 2022, 11 pages.

Sensory Cloud website, nimbus product, Sep. 2, 2019, http://sensory-cloud.com/.

Tanner et al. "Nebulized Isotonic Saline Versus Water Following a Laryngeal Desiccation Challenge in Classically Trained Sopranos", Journal of Speech, Language, and Hearing Research vol. 53, Dec. 2010, pp. 1555-1566.

Van Geffen, et al, "Comparative in-vitro Study of the Trachospray a New Device for Topical Anesthesia of the Upper Airway", Medical Devices: Evidence and Research 2021:14, DovePress, 8 pages.

VanGeffen, et al., "Clinical Evaluation of the trachospray device for upper airway anaesthesia", Anesthesia 2020, Science Letter, 2 pages.

* cited by examiner

APPARATUS FOR USE IN AEROSOL DELIVERY

TECHNICAL FIELD

The present disclosure generally relates to aerosol delivery, and more particularly to apparatus for use in aerosol delivery.

BACKGROUND

Description of the Related Art

It may be useful to delivery an aerosol (e.g., a colloidal suspension of droplets dispersed in air or other gas) into an environment. For instance, it may be useful to dispense an aerosol with in a space or volume (e.g., enclosed volume) in front of or at least partially encloses a nose and/or mouth of a human or other animal to provide a hygienic treatment and/or a therapeutic treatment.

Applicant has described various devices that can provide a hygienic treatment and/or a therapeutic treatment to a human or other animal. For example, International Patent Application Publication WO2019/051403 illustrates and describes a system that employs a nebulizer operable to generate a vapor or aerosol of scent containing droplets having a nominal median size (e.g., 2 microns-50 microns) for retro-nasal delivery. Also for example, International Patent Application Publication WO2020/096686 illustrates and describes a system that employs a nebulizer operable to generate a vapor or aerosol of droplets that include an agonist or antagonist for retro- and/or retro-nasal delivery, the agonist or antagonist including, for example, sodium iodide, sodium chloride, magnesium chloride, capsaicin, piperine, linalool, ground cinnamon, cannabinoid, pimento, onion, clove, thyme, ginger, menthol or TRPV antagonists. Also for example, International Patent Application Publication WO2020/210735 illustrates and describes a thin-profile delivery apparats that employs a nebulizer operable to generate a vapor or aerosol of droplets. Also for example, International Patent Application Publication WO2020/210641 illustrates and describes a system that employs a nebulizer operable to generate a vapor or aerosol of droplets for nominal durations of time. Also for example, International Patent Application Publication WO2020/219921 illustrates and describes a system that employs an actuator such as a nebulizer operable to generate a vapor or aerosol of droplets, for instance into a tumbler.

Current delivery systems for nasal or pulmonary delivery are either separable into discrete parts or comprise an integral whole that is sealed closed and not to be opened by a consumer, patient or end user. The benefits of the latter can include sterility, ability to remain tamper-free, and simplicity. All of the latter devices involve buttons or other triggers that typically expose internal elements of the delivery system to contaminants, for example a crevice, gap or space between a button and an outer casing may allow the ingress of debris or other unwanted material into the interior of the delivery system from an exterior thereof. Such may adversely affect the operation of the delivery system or even contaminate a substance that is delivered by the delivery system.

BRIEF SUMMARY

Applicant has determined that virus shedding (e.g., shedding of the Corona virus such as the various COVID-19 viruses) may be reduced or eliminated via certain hygienic treatments involving certain physiological salts (e.g., Calcium Chloride ($CaCl_2$), Potassium Chloride (KCl)) and/or hydration and/or specific therapeutic agents. Such is described, for example, in U.S. patent application Ser. No. 17/139,401 in which such salts are actively delivered, for instance via an aerosol generated by a nebulizer. Such is also described in U.S. patent application 63/174,713, in which such salts are delivered passively via normal inhalation via a facial mask or component thereof.

It may be advantageous to provide additional forms of devices operable to generate an aerosol, for example devices that are easily transportable, and which do not require a discrete power source (e.g., chemical battery cell, super- or ultra-capacitor), yet which produce an aerosol of droplets with specified characteristics. For example, a delivery device that generates an aerosol of droplets with a median droplet size within a specified range (e.g., equal to or greater than 7 microns, or approximately 9.5 microns or 10 microns, and less than, for example 15 microns). Additionally or alternatively, a delivery device that generates an aerosol of droplets with a specified mass or concentration of humidity and/or salt, or specified mass or volume of humidity and/or salt per unit of time, or specified rate of mass or rate of volume of humidity and/or salt delivery. Such may advantageously allow a device to be provided in a compact form that is easy to carry and use. Such convenience may lead to an increase in frequency of use relative to electrically powered nebulizers. Such may additionally or alternatively advantageously allow a device to deliver humidity and/or salt in a more controlled fashion than that achievable by passive delivery via a facial mask or component thereof. Such may lead to more controlled delivery of the hygienic treatment than otherwise obtainable via a passive face mask. Any one or more of the above mentioned advantages may advantageously lead to a substantial reduction of virus shedding.

Described herein is an apparatus that advantageously has a housing with an interior of the apparatus sealed from an exterior thereof, while still allowing mechanical activation of the apparatus to dispense an aerosol. The aerosol may, for example, take the form of an aerosol that reduces or even eliminates virus shedding. The housing includes two rigid shells and a deformable band (e.g., an elastomer band) that physically couples the rigid shells together for relative translation of the rigid shells with respect to one another, for example in response to a pinching manipulation applied at opposed ends of the housing. Thus, the apparatus advantageously does away with any crevice, gap or space between a housing a button. The housing may have a cavity sized to house a spray bottle which includes a reservoir (e.g., sterile fill reservoir), nozzle and pump or position. Relative translation of the rigid shells with respect to one another actuates the spray bottle to dispense the contents of the reservoir, for example as an aerosol. In at least some implementations, the rigid shells are separable from one another to replace the spray bottle or reservoir via the deformable band. In use, the deformable band prevents ingress of debris or other contaminants into the interior of the housing.

An apparatus for use in aerosol delivery may be summarized as including: a housing comprising: a first rigid shell; a second rigid shell; and a deformable band, the first rigid shell having an outer end, an inner end opposed across a length of the first rigid shell from the outer end of the first rigid shell, the inner end of the first rigid shell having an opening, the second rigid shell having an outer end, an inner end opposed across a length of the second inner shell from the outer end of the second inner shell, the inner end of the second rigid shell having an opening, and the deformable band coupling the inner end of the second rigid shell to the inner end of the first rigid shell with the opening at the inner end of the second inner shell in registration with the opening at the inner end of the first rigid shell, deformation of the band which allows the second rigid shell to axially translate with respect to the first rigid shell along a primary axis of translation, wherein the first ridged shell, the second rigid shell and the band form at least a portion of the housing, the housing having a cavity.

The band can be an elastomer band.

The first rigid shell can have an opening at the outer end of the first rigid shell and the apparatus may include a top cap secured to close the opening at the outer end of the first rigid shell. The first rigid shell can have a port radially offset from the primary axis of translation, and the top cap can have a conduit that is aligned with the port when the top cap is snap fit secured to the first rigid shell via a set of snap fit features. the top cap can have a collar with a receptacle sized to receive an upper portion of a spray bottle when the spray bottle is received in the cavity of the housing and to cooperatively engage an actuator of the spray bottle in response to translation of the first rigid shell relatively toward the second rigid shell along the primary axis of translation when the housing is manipulated by a user.

The second rigid shell can have an opening at the outer end of the second rigid shell and the apparatus may include an end cap, the end cap snap fit secured to close the opening at the outer end of the second rigid shell via a set of snap fit features. The end cap can have an outer face with a concave depression and a bar that extends across the concave depression to allow attachment of a tether.

At least one of the first rigid shell, the second rigid shell or the band can include a set of keyed features sized and positioned to physically engage a set of complementary features of the spray bottle to rotationally align the nozzle of the spray bottle with at least one of the port or the conduit.

the first rigid shell can have an exposed exterior surface that is frustroconical and visible when the apparatus is in use, and the second rigid shell can have an exposed exterior surface that is frustroconical and visible when the apparatus is in use, the exposed exterior surface of the first rigid shell tapering in diameter from the outer end to the inner end thereof and the exposed exterior surface of the second rigid shell tapering in diameter from the outer end to the inner end thereof. The first rigid shell can a neck at the inner end thereof with a respective outer surface having at least one coupler, the second rigid shell can have a neck at the inner end thereof with a respective outer surface having at least one coupler, and the deformable band can have an inner surface with a set of complementary couplers, the at least one coupler of the first rigid shell and the at least one coupler of the second rigid shell are each sized and positioned to detachable mate with respective ones of the complementary couplers of the deformable band.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements are arbitrarily enlarged and positioned to improve drawing legibility. Further, the particular shapes of the elements as drawn, are not necessarily intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with spray bottles, pumps, springs, buttons, triggers, other actuators, and nozzles have not been shown or described in detail to avoid unnecessarily obscuring descriptions of the embodiments.

Unless the context requires otherwise, throughout the specification and claims which follow, the word “comprise” and variations thereof, such as, “comprises” and “comprising” are to be construed in an open, inclusive sense, that is as “including, but not limited to.”

Reference throughout this specification to “one embodiment,” “one implementation,” “an embodiment,” or “an implementation” means that a particular feature, structure or characteristic described in connection with the embodiment or implementation is included in at least one embodiment or one implementation. Thus, the appearances of the phrases “in one embodiment,” “in one implementation,” “in an embodiment,” “or “in one implementation” in various places throughout this specification are not necessarily all referring to the same embodiment or to the same implementation. Furthermore, the particular features, structures, or characteristics may be combined in any suitable manner in one or more embodiments or implementations.

As used in this specification and the appended claims, the singular forms “a,” “an,” and “the” include plural referents unless the content clearly dictates otherwise. It should also be noted that the term “or” is generally employed in its sense including “and/or” unless the content clearly dictates otherwise.

The headings and Abstract of the Disclosure provided herein are for convenience only and do not interpret the scope or meaning of the embodiments.

This disclosure describes various apparatus, methods and articles related to dispensing aerosols, for example aerosols to provide humidification and/or physiological salt(s) and/or mendicants to a human or other animal, preferably having a median droplet size and/or concentration within specified ranges of droplet size and/or concentration.

FIGS. 1, 2, 3, 4, 5, 6, 7, 8 and 9 show an apparatus 10 for use in aerosol delivery, according to at least one illustrated embodiment.

Figure 2:
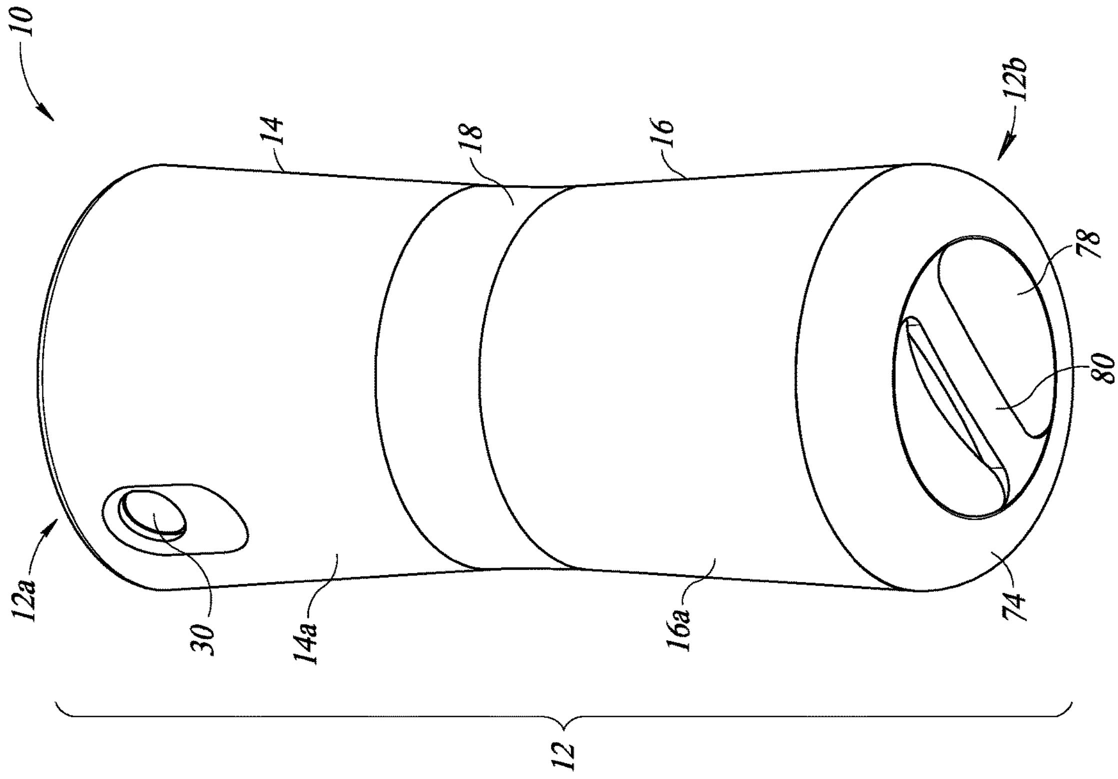
FIG. 2 is a bottom, front, right side isometric view of the apparatus for use in aerosol delivery of FIG. 1.
Figure 1:
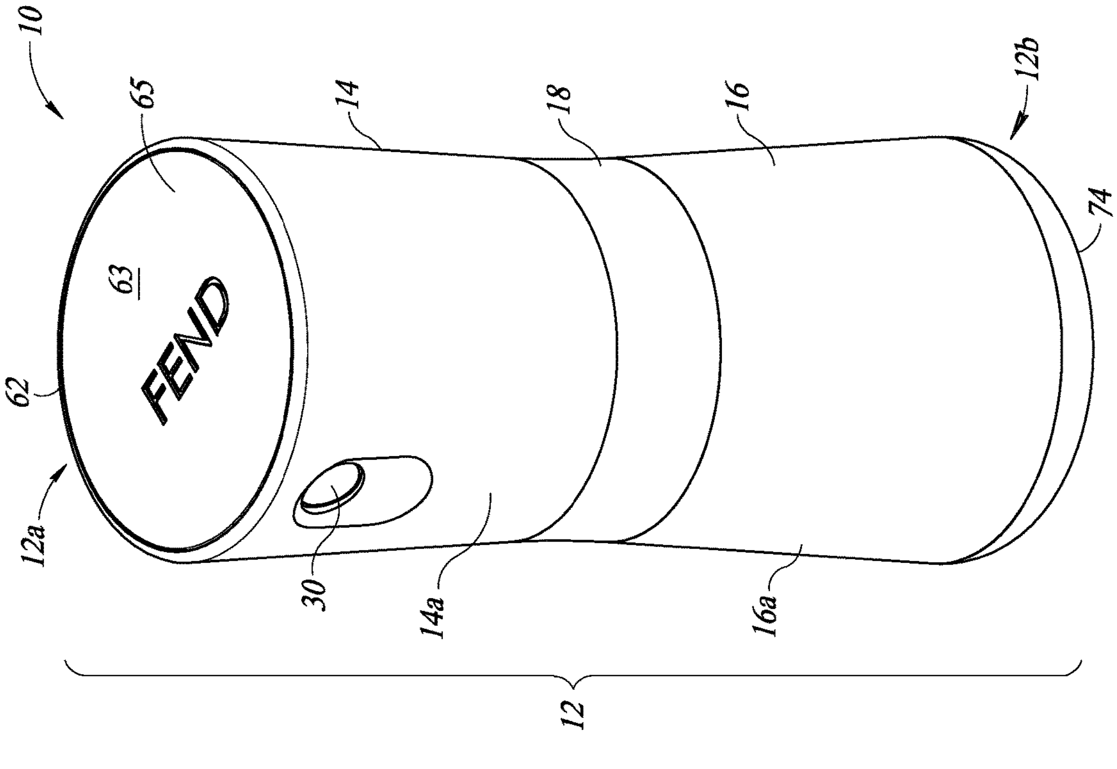
FIG. 1 a top, front, right side isometric view of an apparatus for use in aerosol delivery, according to at least one illustrated embodiment.
Figure 4:
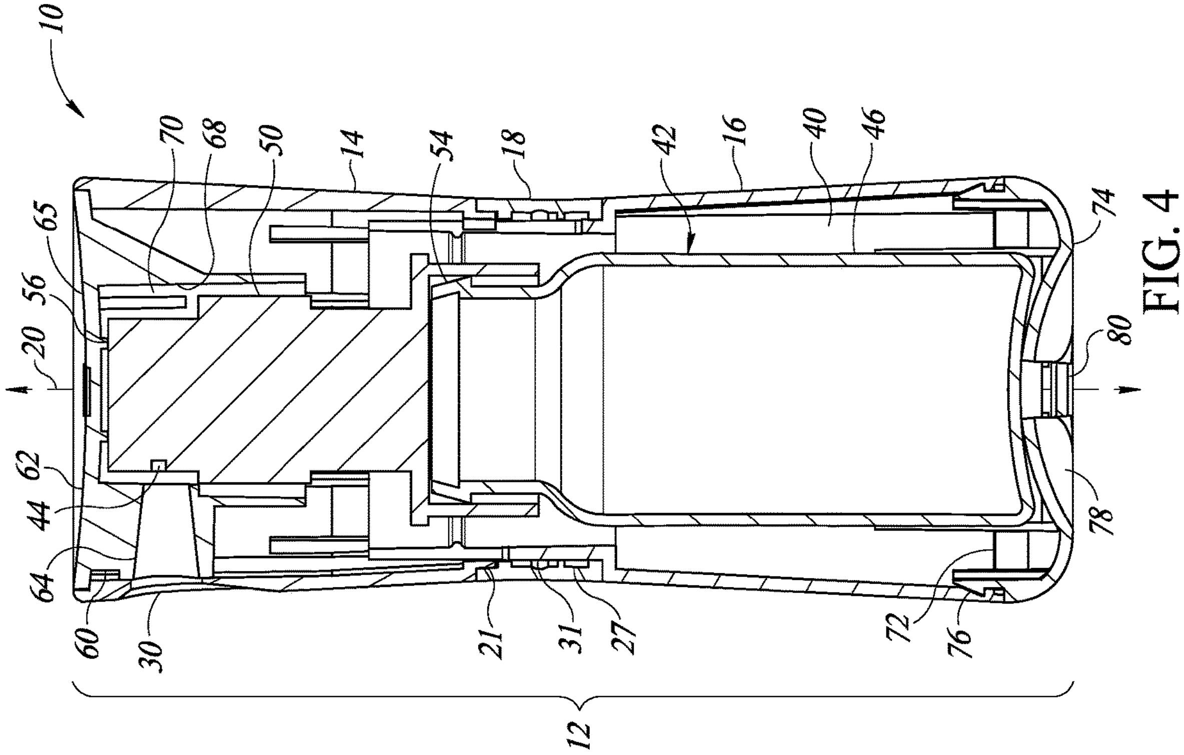
FIG. 4 is a cross-sectional view of the apparatus for use in aerosol delivery of FIG. 3, taken along section line A-A.
Figure 3:
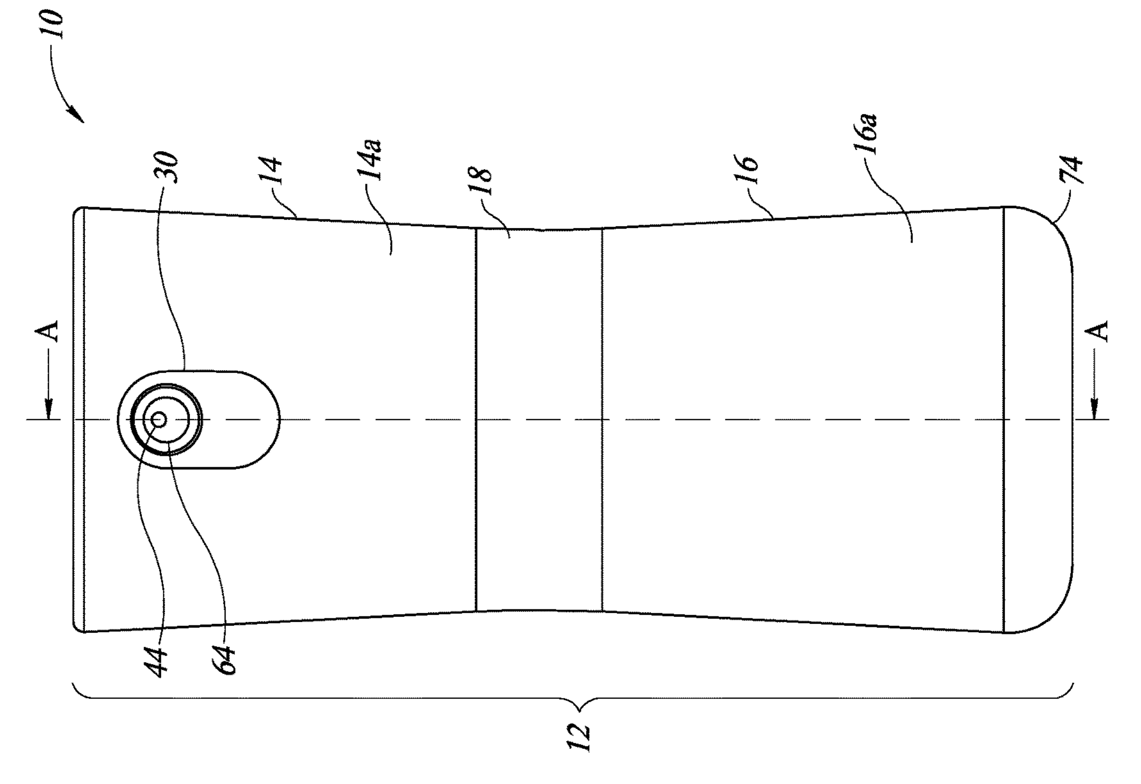
FIG. 3 is a front elevational view of the apparatus for use in aerosol delivery of FIG. 1.

The apparatus 10 comprises a housing 12 having a top 12*a* (called out in FIGS. 1 and 2) and a bottom 12*b* (called out in FIGS. 1 and 2). The housing 12 comprises a first rigid shell 14, a second rigid shell 16, and a deformable band 18 that physically couples the first rigid shell 14 and the second rigid shell 16 together. Deformation of the deformable band 18 allows the second rigid shell 16 to axially translate with respect to the first rigid shell 14 along a primary axis of translation 20 (FIG. 4).

The first rigid shell 14 has an outer end 22 (called out in FIG. 9) and an inner end 24 (called out in FIG. 9) opposed across a length 26 (called out in FIG. 9) of the first rigid shell 14 from the outer end 22 of the first rigid shell 14. The inner end 24 of the first rigid shell 14 has an opening 28 (called out in FIG. 9). The first rigid shell 14 has a port 30, the port 30 radially offset from the primary axis of translation 20 (called out in FIG. 4) to provide a passage that extends generally perpendicularly to the primary axis of translation 20.

In at least some implementations, the first rigid shell 14 has a collar 21 at the inner end 24 thereof with a respective outer surface 23 having at least one coupler 25 (e.g., thread, male thread, female thread, ridge(s), detent(s), lip(s), recess(es), bayonet mount). In at least some implementations, the deformable band 18 has an inner surface 27 with a set of complementary couplers 29 (e.g., thread, male thread, female thread, ridge(s), detent(s), lip(s), recess(es), bayonet mount), the at least one coupler 25 of the first rigid shell 14 sized and positioned to detachable mate with respective ones of the complementary couplers 29 (e.g., thread, ridge, detent, lip, recess) of the deformable band 18. The collar 21 may be dimensioned to be received (e.g., closely received) by the deformable band 18. For example, an outer diameter (OD) of the collar 21 may have dimensions that are equal to or less than an inner diameter (ID) of the deformable band 18.

The first rigid shell 14, other than the port 30, may, for example, take the form of a body of revolution. For instance, the first rigid shell 14 can have an exposed exterior surface 14*a* that is frustroconical and visible when the apparatus 10 is in use, the frustroconical shape tapering in diameter from the outer end 22 of the first rigid shell 14 to the inner end 24 of the first rigid shell 14.

The exposed exterior surface 14*a* may have dimensions to present a generally smooth mating with an exposed exterior surface of the deformable band 18. For example, an outer diameter (OD) of the exposed exterior surface 14*a* at the inner end 22 may have dimensions that are equal to an outer diameter (OD) of the deformable band 18.

The second rigid shell 16 has an outer end 32 (called out in FIG. 9) and an inner end 34 (called out in FIG. 9) opposed across a length 36 (called out in FIG. 9) of the second inner shell 16 from the outer end 32 of the second inner shell 16. The inner end 34 of the second rigid shell 16 has an opening 38 (called out in FIG. 9).

In at least some implementations, the second rigid shell 16 has a collar 31 (called out in FIG. 9) at the inner end 34 thereof with a respective outer surface 33 having at least one coupler 35 (e.g., thread, ridge, detent, lip, recess). In at least some implementations, the deformable band 18 has an inner surface 27 with a set of complementary couplers 29 (e.g., thread, ridge, detent, lip, recess), the at least one coupler 35 of the second rigid shell 16 sized and positioned to detachable mate with respective ones of the complementary couplers 29 of the deformable band 18. The collar 31 may be dimensioned to be received (e.g., closely received) by the deformable band 18. For example, an outer diameter (OD) of the collar 31 may have dimensions that are equal to or less than an inner diameter (ID) of the deformable band 18.

The second rigid shell 16, may, for example, take the form of a body of revolution. For instance, the second rigid shell 16 can have an exposed exterior surface 16*a* that is frustroconical and visible when the apparatus 10 is in use, the frustroconical shape tapering in diameter from the outer end 32 of the second rigid shell 16 to the inner end 34 of the second rigid shell 16.

The exposed exterior surface 16*a* may have dimensions to present a generally smooth mating with an exposed exterior surface of the deformable band 18. For example, an outer diameter (OD) of the exposed exterior surface 16*a* at the inner end 32 may have dimensions that are equal to an outer diameter (OD) of the deformable band 18.

The first and the second rigid shells 14, 16 of the housing 12 may be made of plastic, for example injection molded plastic. Alternatively, the first and the second rigid shells 14, 16 of the housing 12 may be made of metal, preferably a non-ferrous metal which may be a powder coated metal or an anodized metal.

The deformable band 18 couples the inner end 34 of the second rigid shell 16 to the inner end 24 of the first rigid shell 14 with the opening 38 at the inner end 34 of the second inner shell 16 in registration with the opening 28 at the inner end 24 of the first rigid shell 14 (e.g., centered on the same axis, with or without matching dimensions or overlapping perimeters). The deformable band 18 may, for example, take the form of an elastomer band (e.g., thermoplastic rubber or elastomer (TPE) band), which may be resiliently deformable. When coupled together, the first rigid shell 14, the second rigid shell 16 and the deformable band 18 can optionally provide a generally hourglass shape exterior surface 14*a*, 16*a* which is visible when in use.

Figure 6:
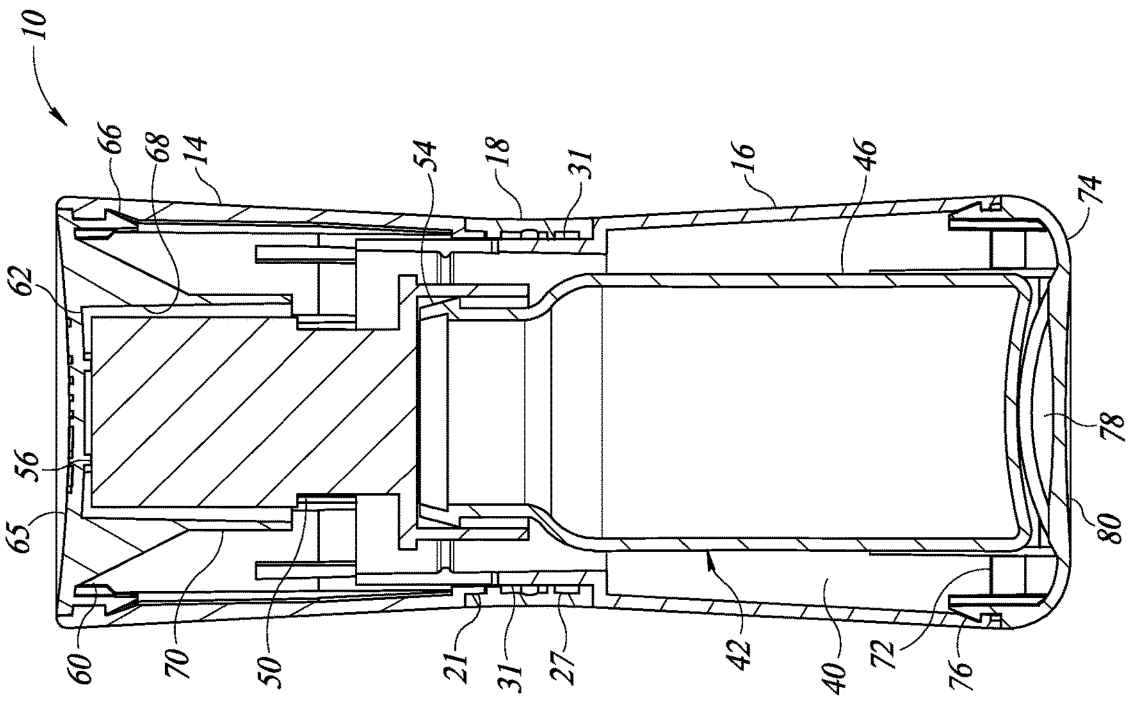
FIG. 6 is a cross-sectional view of the apparatus for use in aerosol delivery of FIG. 4, taken along section line B-B.
Figure 5:
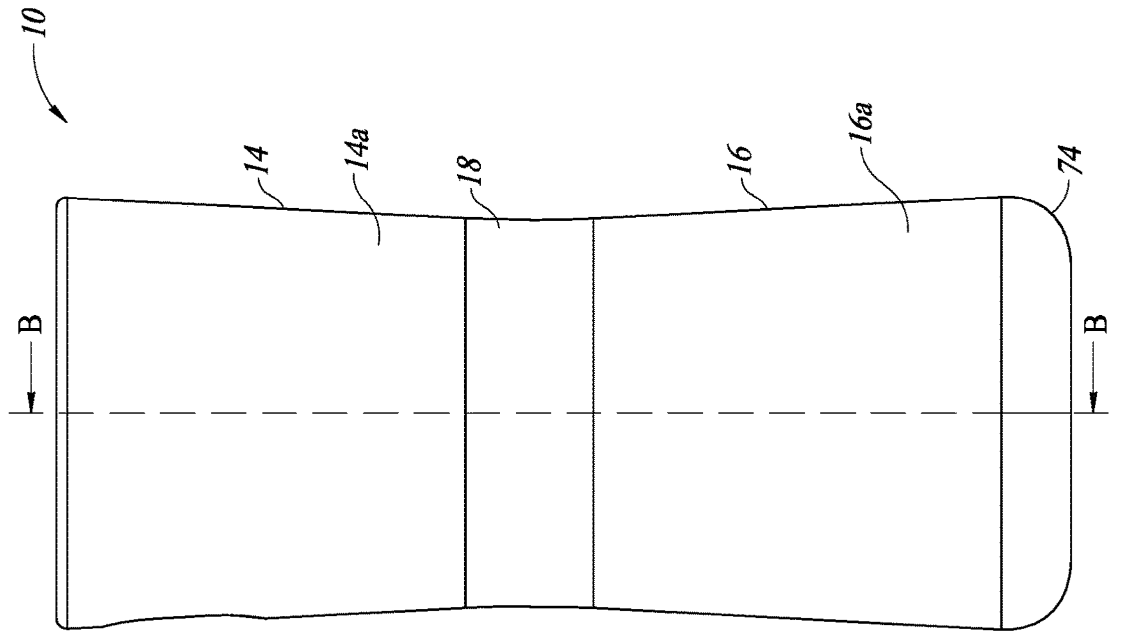
FIG. 5 is a rear elevational view of the apparatus for use in aerosol delivery of FIG. 1.
Figure 7:
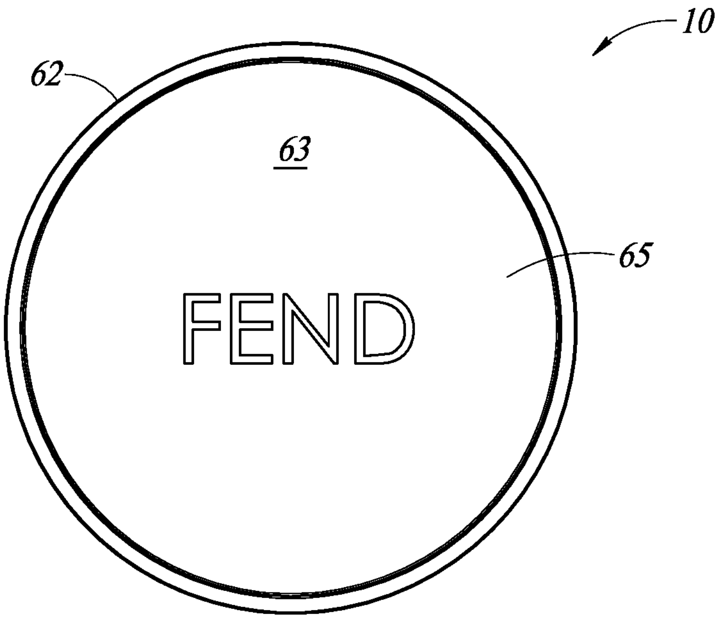
FIG. 7 is a top plan view of the apparatus for use in aerosol delivery of FIG. 1.
Figure 8:
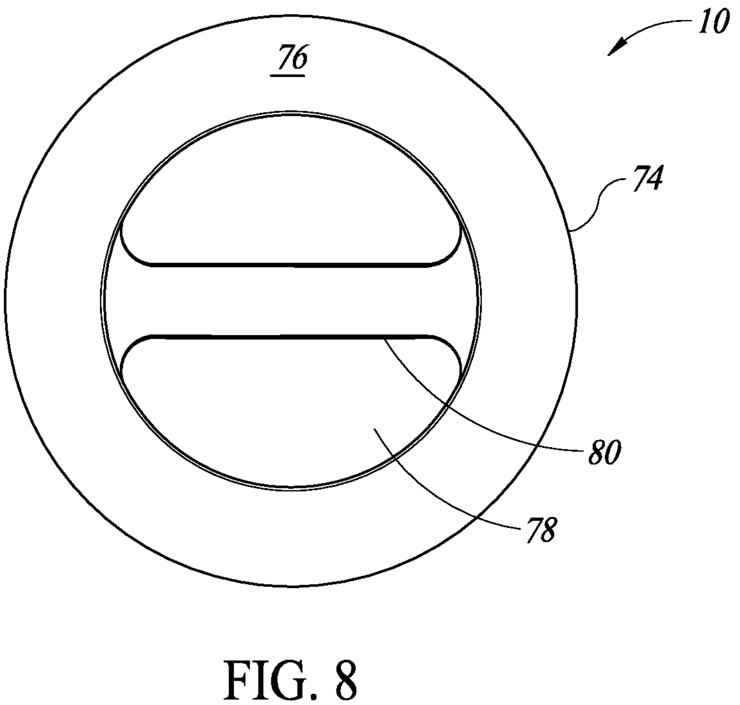
FIG. 8 is a bottom plan view of the apparatus for use in aerosol delivery of FIG. 1.
Figure 9:
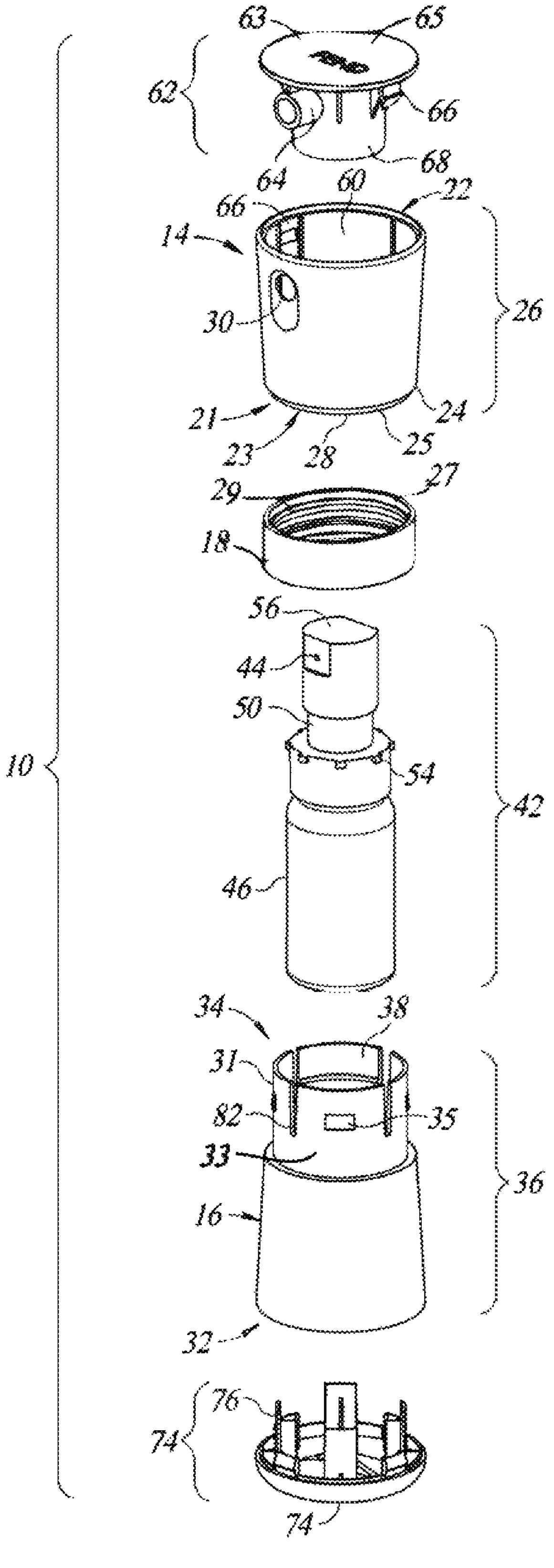
FIG. 9 is a top, front, right side exploded view of the apparatus for use in aerosol delivery of FIG. 1.

When coupled together, the first rigid shell 14, the second rigid shell 16 and the deformable band 18 form at least a portion of the housing 12, the housing having a cavity 40 (called out in FIGS. 4 and 6). The cavity 40 of the housing 12 is sized and/or shaped to hold a spray bottle 42 (visible in FIGS. 4, 6 and 9).

The apparatus 10 may optionally include the spray bottle 42, the spray bottle 42 received in cavity 40 of the housing 12. The spray bottle 42 is preferably removably received in cavity 40 of the housing 12, for example via separation of at least one of the first rigid shell 14 or the second rigid shell 16 from one another via the deformable band 18.

Figure 10:
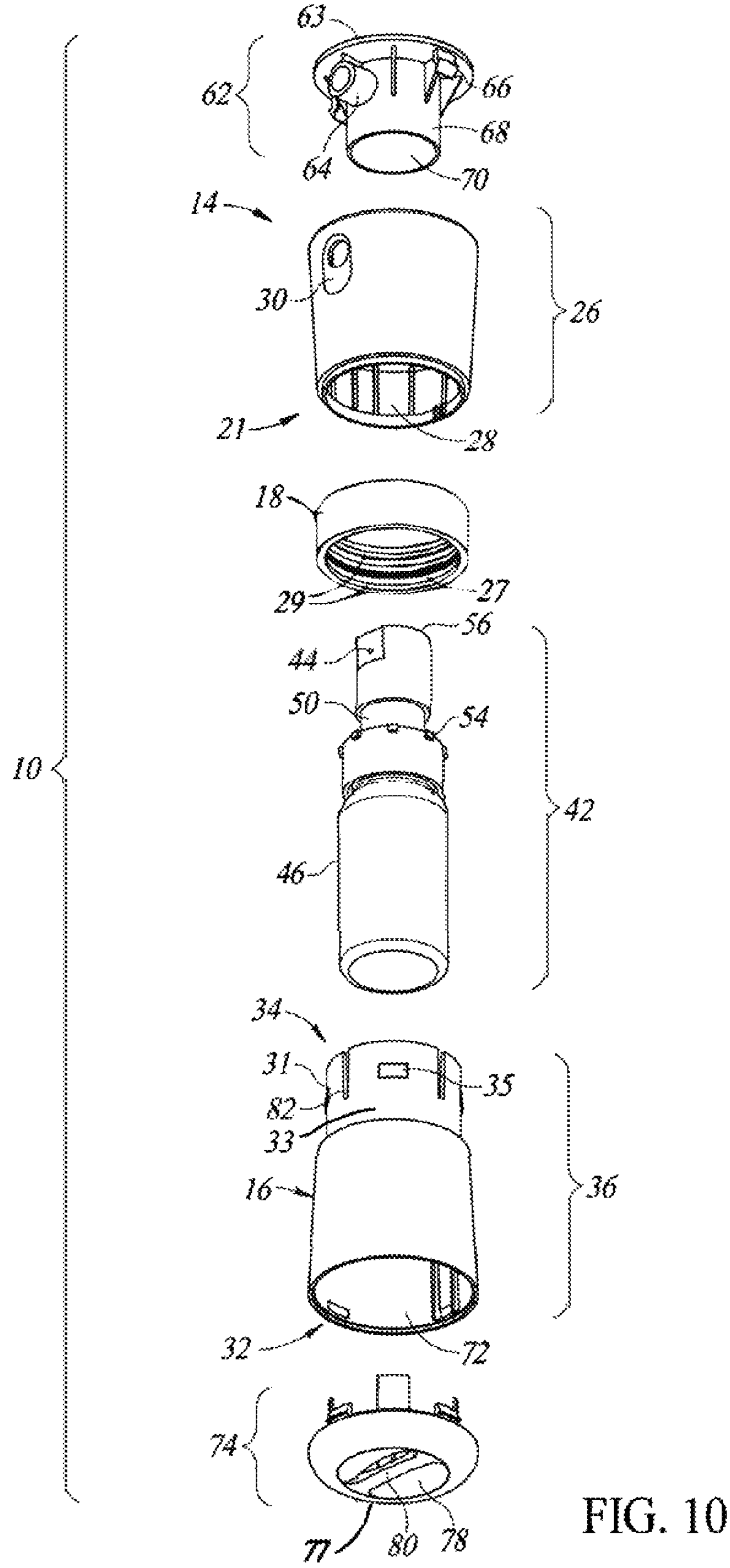
FIG. 10 is a bottom, front, right side exploded view of the apparatus for use in aerosol delivery of FIG. 1.

In at least some implementations, the spray bottle 42 comprises: a nozzle 44 (called out in FIGS. 4 and 9), a reservoir 46 to hold a fluid, a check valve (not visible) fluidly communicatively coupled to control fluid flow with respect to the reservoir 46 and the nozzle 44, a piston or pump 50, and a spring (not visible), wherein the piston or pump 50 is operable to draw fluid from the reservoir 46 in response to an actuation against a biasing force of the spring to deliver the aerosol via the nozzle 44. In at least some implementations, the spray bottle 42 also comprises a draw tube (not visible). In at least some implementations, the spray bottle 42 also comprises one or more registration features 54 (called out in FIGS. 9 and 10), for example slots and pins. In at least some implementations, the spray bottle 42 further comprises an actuator (e.g., button, trigger) 56. The actuator 56 can, for example, be translatable along the principal axis of translation 20 of the first rigid shell 14 and the second rigid shell 16 in response to translation of the second rigid shell 16 with respect to the first rigid shell 14 to cooperative engage the piston or pump 50.

The spray bottle 42 may have one or more flats (not shown). An interior of at least a portion of the housing 12 may have one or more flats (not shown), sized and positioned to engage the flat(s) on the spray bottle 42 to rotationally orient the nozzle 44 of the spray bottle 42 with the port of the first rigid shell 14 and limit or prevent rotation of the spray bottle 42 at least when no opening or closing the housing 12. For example, the spray bottle 42 and interior of at least a portion of the housing 12 may each have a D-shaped profile, rectangular profile, or a hexagonal profile.

The first rigid shell 14 may optionally have an opening 60 at the outer end 22 of the first rigid shell 14. The apparatus 10 may optionally include a top cap 62, the top cap 62 secured to close the opening 60 at the outer end 22 of the first rigid shell 14. The top cap 62 has a top surface 63 that fits in and/or over the opening 60 to close the opening 60. The top surface 63 may be concave or have a concavity 65 sized to accommodate a portion of a digit (e.g., distal phalange of thumb or index finger). The top cap 62 optionally has a conduit 64 that is aligned with the port 30 when the top cap 62 is snap fit secured to the first rigid shell 14 via a set of snap fit features 66 (only one called out in FIG. 9), e.g., detent, lip, protrusion. The top cap 62 has a collar 68 with a receptacle 70 (called out in FIGS. 4, 6 and 10) sized to receive an upper portion of the spray bottle 42 when the spray bottle 42 is received in the cavity 40 of the housing 12 and to cooperatively engage an actuator 56 of the spray bottle 42 in response to translation of the first rigid shell 14 relatively toward the second rigid shell 16 along the primary axis of translation 20 when the housing 12 is manipulated by a user.

The second rigid shell 16 has an opening 72 (called out in FIGS. 4, 6 and 10) at the outer end 32 of the second rigid shell 16. The apparatus 10 may optionally include an end cap 74, the end cap 74 snap fit secured to close the opening 72 at the outer end 32 of the second rigid shell 16 via a set of snap fit features 76 (only one called out in FIG. 9), e.g., detent, lip, protrusion. The end cap 74 has an outer face 77 with a concave depression 78 (called out in FIGS. 4, 6 and 9) and a bar 80 (called out in FIGS. 4, 6 and 9) that extends across the concave depression 78 with a space therebetween to allow attachment of a tether (e.g., lanyard).

In at least some implementations, at least one of the first rigid shell 14, the second rigid shell 16 and/or the deformable band 18 includes a set of keyed features 82 (called out in FIG. 9), e.g., slots, sized and positioned to physically engage a set of complementary registration features 54 (e.g., radially extending tabs) of the spray bottle 42 to rotationally align the nozzle 44 of the spray bottle 42 with at least one of the port 30 of the first rigid shell 14 and/or the conduit 64 of the top cap 62.

In at least some implementations, at least one of the top cap 62 or the end cap 74 is removably coupleable to alternatively open and close the opening 60, 72 at the outer end 22 of the first rigid shell 14 or the outer end 32 of the second rigid shell 16.

In use, the reservoir 46 may hold a fluid (e.g., a liquid) that includes water and/or one or more physiological salts, and the apparatus 10 used to generate an aerosol to hydrate and/or provide physiological salts to the upper respiratory tract of a human or other animal. The reservoir 46 may advantageously take the form of a sterile fill reservoir, (e.g., a reservoir having a sterile interior, that is filled with a sterilized fluid in a sterilized environment and hermetically sealed to maintain the sterile condition within the reservoir 46), advantageously allowing the omission of preservatives and/or specific pH conditions otherwise employed to preserve the sterility of the fluid composition in the reservoir 46. The physiological salts may, for example, consist of calcium chloride, comprise calcium chloride, consist of potassium chloride, comprise potassium chloride, consist of sodium chloride, comprise sodium chloride and/or omit sodium chloride. The nozzle 44 may be designed to achieve a nominal median droplet size, for example from 7 microns to approximately 15 microns, or 9.5 microns or 10 microns, to substantially retain the aerosol in the upper respiratory tract. Size, dosing and compositions or formulations are generally described in U.S. patent application Ser. No. 17/139,401; and U.S. patent application 63/174,713, the contents of which are incorporated herein by reference in their entirety. The piston or pump 50 may be sized to deliver a full measured effective dose on each activation or a full measured effective dose on a defined whole number of activations of the actuator 56 (e.g., four successive squeezes of the housing to engage the actuator 56 four times). For example, a user may position digits on either end of the apparatus 10, for instance a thumb on a bottom end and an index finger of the same hand on a top end of the housing (e.g., on the end cap 74 and the top cap 62). The user may then pinch the index finger and thumb together, causing the first and the second rigid shells 14, 16 to be drawn together, and activating the piston or pump 50 to cause a spray of aerosol to be dispensed via the nozzle 44.

When the fluid in the reservoir 46 is depleted, the housing 12 can be opened, for example by separating or decoupling one or both of the first and second rigid shells 14, 16 from the deformable band 18, the spent spray bottle 42 removed and a new spray bottle inserted into the cavity 40. In at least some implementations, the housing 12 may be opened by twisting or rotating the first rigid shell 14 relative to the and second rigid shell 16, for example about primary axis of translation 20 (e.g., where coupler and/or complimentary coupler are a male thread and female thread sized and positioned to securely engage one another. The housing 12 can then be closed, for example by joining or coupling one or both of the first and second rigid shells 14, 16 to the deformable band 18, and used in the fashioned described above.

U.S. Provisional Patent Application No. 63/211,633, filed Jun. 17, 2021 is hereby incorporated herein by reference, in its entirety.

The various embodiments described above can be combined to provide further embodiments. Aspects of the embodiments can be modified, if necessary, to employ systems, circuits and concepts of the various patents, applications and publications identified herein to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. An apparatus for use in aerosol delivery, the apparatus comprising:

a housing comprising: a first rigid shell; a second rigid shell; and a deformable band, the first rigid shell having an outer end, an inner end opposed across a length of the first rigid shell from the outer end of the first rigid shell, the inner end of the first rigid shell having an opening, the second rigid shell having an outer end, an inner end opposed across a length of the second inner shell from the outer end of the second inner shell, the inner end of the second rigid shell having an opening, and the deformable band coupling the inner end of the second rigid shell to the inner end of the first rigid shell with the opening at the inner end of the second inner shell in registration with the opening at the inner end of the first rigid shell, deformation of the deformable band which allows the second rigid shell to axially translate with respect to the first rigid shell along a primary axis of translation, wherein the first rigid shell, the second rigid shell and the deformable band form at least a portion of the housing, the housing having a cavity.

2. The apparatus of claim 1 where the deformable band is an elastomer band.

3. The apparatus of claim 2 wherein the first rigid shell has an opening at the outer end of the first rigid shell; and further comprising:

a top cap secured to close the opening at the outer end of the first rigid shell.

4. The apparatus of claim 3 wherein the first rigid shell has a port radially offset from the primary axis of translation, and the top cap has a conduit that is aligned with the port when the top cap is snap fit secured to the first rigid shell via a set of snap fit features.

5. The apparatus of claim 4 where the top cap has a collar with a receptacle sized to receive an upper portion of a spray bottle when the spray bottle is received in the cavity of the housing and to cooperatively engage an actuator of the spray bottle in response to translation of the first rigid shell relatively toward the second rigid shell along the primary axis of translation when the housing is manipulated by a user.

6. The apparatus of claim 4 wherein at least one of the first rigid shell, the second rigid shell or the deformable band includes a set of keyed features sized and positioned to physically engage a set of complementary features of a spray bottle to rotationally align the nozzle of the spray bottle with at least one of the port or the conduit.

7. The apparatus of claim 1 wherein the second rigid shell has an opening at the outer end of the second rigid shell, and further comprising:

an end cap, the end cap snap fit secured to close the opening at the outer end of the second rigid shell via a set of snap fit features.

8. The apparatus of claim 7 where the end cap has an outer face with a concave depression and a bar that extends across the concave depression to allow attachment of a tether.

9. The apparatus of claim 1 wherein the first rigid shell has an exposed exterior surface that is frustroconical and visible when the apparatus is in use, and the second rigid shell has an exposed exterior surface that is frustroconical and visible when the apparatus is in use, the exposed exterior surface of the first rigid shell tapering in diameter from the outer end to the inner end of the first rigid shell and the exposed exterior surface of the second rigid shell tapering in diameter from the outer end to the inner end of the second rigid shell.

10. The apparatus of claim 9 wherein the first rigid shell has a neck at the inner end of the first rigid shell with a respective outer surface having at least one coupler, the second rigid shell has a neck at the inner end of the second rigid shell with a respective outer surface having at least one coupler, and the deformable band has an inner surface with a set of complementary couplers, the at least one coupler of the first rigid shell and the at least one coupler of the second rigid shell are each sized and positioned to detachable mate with respective ones of the complementary couplers of the deformable band.

11. The apparatus of claim 10 wherein the cavity is sized to accommodate a spray bottle.

12. The apparatus of claim 1 wherein the cavity is sized to accommodate a spray bottle.

13. The apparatus of claim 1, further comprising:

a spray bottle, the spray bottle received in the cavity of the housing.

14. The apparatus of claim 13 wherein the spray bottle is removably received in the cavity of the housing via separation of at least one of the first rigid shell or the second rigid shell from one another via the deformable band.

15. The apparatus of claim 14 wherein the spray bottle comprises:

a nozzle;

a sterile fill reservoir to hold a fluid;

a check valve fluidly communicatively coupled to control fluid flow with respect to the sterile fill reservoir and the nozzle;

a piston; and a spring, wherein the piston is operable to draw fluid from the sterile fill reservoir in response to an actuation against a biasing force of the spring to deliver the aerosol via the nozzle.

16. The apparatus of claim 15 wherein the spray bottle further comprises an actuator, the actuator translatable along the primary axis of translation of the first and the second rigid shells in response to translation of the second rigid shell with respect to the first rigid shell.

17. The apparatus of claim 1 wherein at least one of the first rigid shell or the second rigid shell has an opening at the outer end thereof, and further comprising:

an end cap that is removably coupleable to alternatively open and close the opening at the outer end of the first rigid shell or the second rigid shell.

18. An apparatus for use in aerosol delivery, the apparatus comprising a spray bottle having a reservoir of fluid, a nozzle, a pump, and a translatable cap, translation of the translatable cap actuates the pump to cause fluid to be dispersed via the nozzle; and a housing comprising: a first rigid shell; a second rigid shell; and an elastomer band, the first rigid shell having an outer end, an inner end opposed across a length of the first rigid shell from the outer end of the first rigid shell, the inner end of the first rigid shell having an opening, the second rigid shell having an outer end, an inner end opposed across a length of the second inner shell from the outer end of the second inner shell, the inner end of the second rigid shell having an opening, and the elastomer band coupling the inner end of the second rigid shell to the inner end of the first rigid shell with the opening at the inner end of the second inner shell in registration with the opening at the inner end of the first rigid shell, deformation of the elastomer band which allows the second rigid shell to axially translate with respect to the first rigid shell along a primary axis of translation, wherein the first rigid shell, the second rigid shell and the elastomer band at least partially delineate a cavity of the housing, the cavity sized to receive the spray bottle therein and at least a portion of the housing cooperatively engages at least a portion of the spray bottle to cause actuation of the pump in response to translation of the second rigid shell relative to the first rigid shell.

19. The apparatus of claim 18 wherein the first rigid shell has a port radially offset from the primary axis of translation and the first rigid shell has an opening at the outer end of the first rigid shell, and the second rigid shell has an opening at the outer end of the second rigid shell; and further comprising:

a top cap having a conduit, a collar, and a set of snap fit features, the collar having a receptacle sized to receive the translatable cap of the spray bottle when the spray bottle is received in the cavity of the housing and to cooperatively engage the translatable cap of the spray bottle in response to translation of the first rigid shell relatively toward the second rigid shell along the primary axis of translation when the housing is manipulated, the top cap secured to close the opening at the outer end of the first rigid shell with the conduit aligned with the port when the top cap is snap fit secured to the first rigid shell; and an end cap, the end cap snap fit secured to close the opening at the outer end of the second rigid shell via a set of snap fit features.

20. The apparatus of claim 18 wherein the reservoir of fluid is a sterile fill reservoir, and the first rigid shell has an exposed exterior surface that is frustroconical and visible when the apparatus is in use, and the second rigid shell has an exposed exterior surface that is frustroconical and visible when the apparatus is in use, the exposed exterior surface of the first rigid shell tapering in diameter from the outer end to the inner end of the first rigid shell and the exposed exterior surface of the second rigid shell tapering in diameter from the outer end to the inner end of the second rigid shell, and the first rigid shell has a neck at the inner end of the first rigid shell with a respective outer surface having at least one coupler, the second rigid shell has a neck at the inner end of the second rigid shell with a respective outer surface having at least one coupler, and the elastomer band has an inner surface with a set of complementary couplers, the at least one coupler of the first rigid shell and the at least one coupler of the second rigid shell are each sized and positioned to detachable mate with respective ones of the complementary couplers of the elastomer band.

* * * * *